(12) United States Patent
Kirsch

(10) Patent No.: US 6,870,367 B2
(45) Date of Patent: Mar. 22, 2005

(54) MAGNETIC RESONANCE IMAGING (MRI) WITH CONTINUOUS TABLE MOTION

(75) Inventor: Rainer Kirsch, Berlin (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 10/760,050

(22) Filed: Jan. 16, 2004

(65) Prior Publication Data

US 2004/0207401 A1 Oct. 21, 2004

(30) Foreign Application Priority Data

Jan. 16, 2003 (DE) .......................... 103 01 497

(51) Int. Cl.$^7$ ................................................. G01V 3/00
(52) U.S. Cl. ..................................... 324/309; 324/307
(58) Field of Search ................................ 324/309, 307, 324/311, 314, 318, 319, 322

(56) References Cited

U.S. PATENT DOCUMENTS

| | | |
|---|---|---|
| 5,631,560 A | 5/1997 | Machida |
| 6,707,300 B2 * | 3/2004 | Polzin et al. ............... 324/309 |
| 6,794,869 B2 * | 9/2004 | Brittain ....................... 324/309 |
| 2002/0173715 A1 | 11/2002 | Kruger et al. |

FOREIGN PATENT DOCUMENTS

EP 1 024 371 8/2000

* cited by examiner

*Primary Examiner*—Brij B. Shrivastav
(74) *Attorney, Agent, or Firm*—Schiff Hardin LLP

(57) ABSTRACT

In a magnetic resonance imaging method and apparatus and computer program product, spatial scanning of a block-shaped volume of a patient is undertaken by applying a phase-coding gradient in a slice selection direction, as well as by applying a frequency-coding gradient in a plane vertical to the direction of the phase-coding gradient. The body is uniformly and continuously moved by uniformly and continuously moving a table on which the body is situated until the block-shaped volume moves uniformly through the homogeneity volume of the magnetic resonance apparatus. The gradient fields are simultaneously uniformly continuously shifted in conformity with the motion of the table, so that the block-shaped volume being scanned does not move in relation to the table, and thus does not move in relation to the patient, until the block-shaped volume proceeds through the entirety of the homogeneity volume, and scanning is completed.

7 Claims, 6 Drawing Sheets

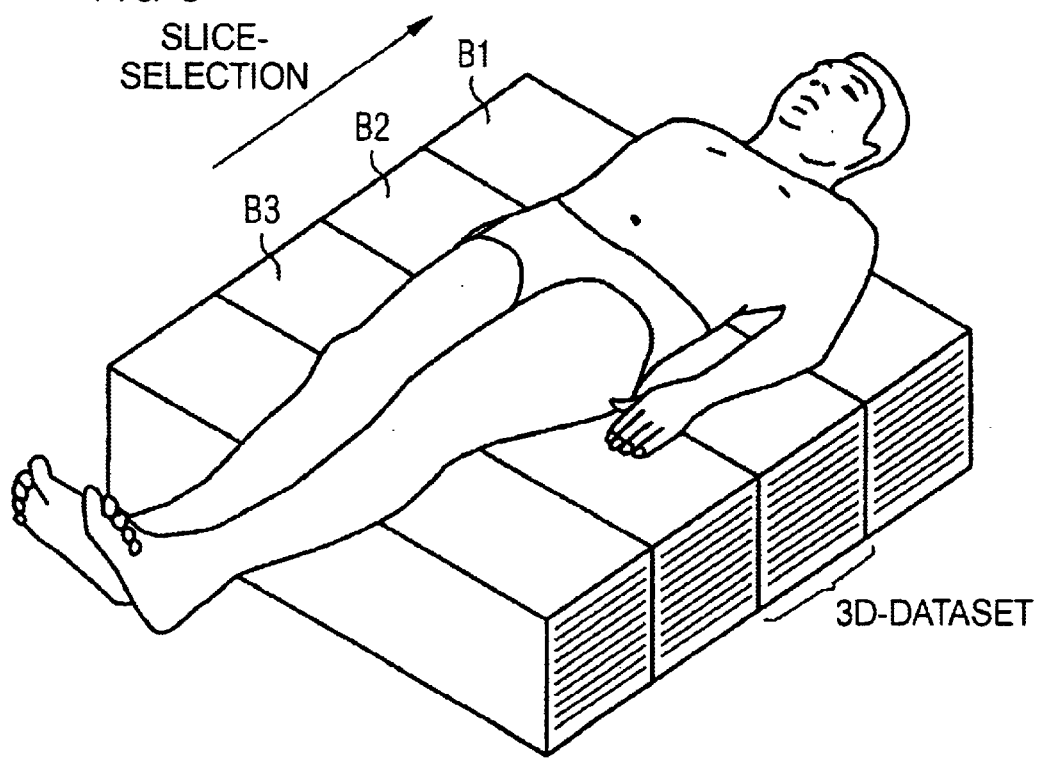
FIG 3
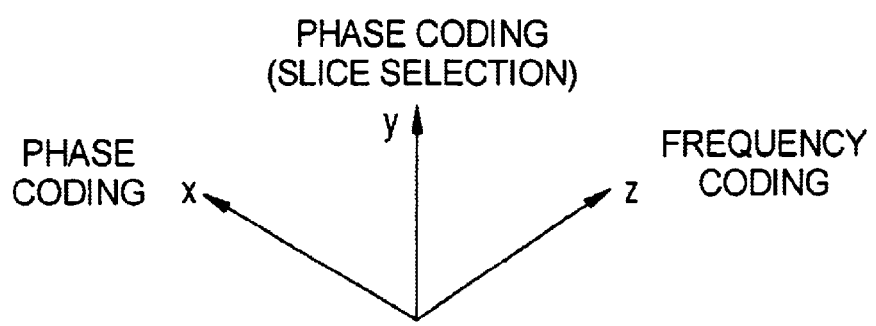

MAGNETIC RESONANCE IMAGING (MRI) WITH CONTINUOUS TABLE MOTION

BACKGROUND OF THE INVENTION

1. Field of the Invention

The present invention relates generally to magnetic resonance imaging (MRI), also known as magnetic resonance tomography (MRT) as applied in medicine to examine patients.

2. Description of the Prior Art

MRI is based on the physical phenomenon of nuclear magnetic resonance and has been successfully used as an imaging procedure in medicine and in biophysics for over 15 years. Using this examination modality, the patient is exposed to a strong, constant magnetic field. This causes the nuclear spins of atoms in the object (which were previously randomly oriented) to align in a certain direction. Radio-frequency energy can then excite the aligned nuclear spins to a certain oscillation. It is this oscillation that generates in the MRI system the actual measurement signal, which is then received using suitable reception coils. Using spatially linearly variable magnetic fields generated by gradient coils, the examination subject can be spatially encoded in all three directions in space, which is generally called "location coding".

The acquisition of data in an MRI system occurs in so-called k-space (frequency domain). The MRI image in the "field-of-view" is associated with the MRI data in k-space by Fourier transformation. The location coding of the object, which encompasses (fills) k-space, occurs by means of gradients in all three directions in space. In doing so, a distinction is made among layer selection (defines an acquisition layer in the object, e.g., the Z-axis), frequency coding (defines a direction within the layer, e.g., the x-axis), and phase-coding (defines the second dimension within the layer, e.g., the y-axis). In addition, during the 3D imaging the phase-coding can subdivide the selected layer in partitions, e.g., along the z-axis.

Thus, first a layer is selectively excited, e.g., in the z-direction, and—if need be—a phase coding in, e.g., the x-direction can be performed. The encoding of the location information in the layer is done by a combination of phase and frequency coding by means of the two previously mentioned orthogonal gradient fields that (in the example of the layer being excited in the z-direction) are generated by the gradient coils in the x- and y-directions.

In order to scan a whole layer of a subject to be surveyed, the imaging sequence (e.g., the gradient echo sequence, FLASH) is repeated n times for various values of the phase-coding gradient, e.g., $G^y$. At each sequence, the magnetic resonance signal (e.g., gradient echo signal) is scanned, digitized, and stored by a $\Delta t$-pulsed ADC (Analog Digital Converter), which is also done n times in equidistant time steps $\Delta t$ in the presence of the selective gradient $G^F$. In this manner, a number matrix is created in individual rows (a matrix in k-space, i.e., a k-matrix) with N×N data points. By Fourier transformation, this set of data allows an MR image of the scanned plane to be reconstructed with a resolution of N×N pixels (a symmetrical matrix with N×N points is only an example; asymmetrical matrices also can be generated). The values in the region of the center of the k-matrix contain primarily information about the contrast, and the values in the peripheral area of the k-matrix tend to contain information regarding the resolution of the transformed MRI image.

MRI also allows sectional images of the human body to be acquired in all directions. MRI as a sectional imaging procedure in the practice of medical diagnostics is characterized, above all, as a non-invasive examination method. In spite of this defining feature, angiographic images (i.e., images of the blood vessels in the human body, particularly those in the organs with sufficient blood supply) are limited in terms of their contrast in the generic MR imaging process; these limits, however, can be substantially overcome with the use of contrast agents. The effect of contrast agents is generally based on influencing the parameters that are decisive for the contrast, such as the longitudinal or transversal relaxation time $T_1$ or $T_2$. The substance most often used in clinical practice is trivalent gadolinium $Gd^{3+}$, which has a T1-shortening effect. Binding in the so-called chelate complexes (DTPA, Diethylene Triamine Pentaacetic Acid) causes gadolinium to lose its toxicity so that Gd DTPA usually can be applied by means of intravenous administration. The operator selects a vein that leads directly to the heart, which then distributes the contrast agent throughout the entire arterial system—usually from the aortic arch to the toes. In the sequences that are generally used (T1-weighted spin echo sequence, gradient echo sequence, etc.), the accelerated T1 relaxation causes an enhancement of the MR signal; it is a lighter representation of the relevant tissue in the MR image. In this manner, sharp, rich-in-contrast images of, for example, head, neck, heart, or kidney vessels can be obtained.

Such procedure based on the use of a contrast agent in the magnetic resonance imaging is generally called "Contrast-Enhanced MR Angiography (CE MRA). The quality of the contrast agent based vessel images depends largely on the temporal co-ordination of the sequence steps characterizing the scanning, which is generally called timing or contrast agent timing. The basic sequence steps are: contrast agent injection, a writing time, and scanning of the center of the k-space matrix. In order to achieve the best possible contrast of the image, the center region of the k-matrix should be scanned when the contrast agent is present in the area of interest (field of view—FOV) in a maximum concentration. For this reason, according to the current state-of-the-art the contrast-enhanced angiography is performed as follows:

A contrast agent is injected intravenously into the patient's body, which then gets distributed through the heart in the arterial vessel system—especially from the aortic arch to the toes. After the contrast agent is properly distributed, the individual sections of interest of the subject are excited one after another. After a section has been scanned, the patient is shifted while lying on a movable table by the width of the section, and a new body section of the same dimensions is excited and scanned. The scanning of a 3D section of a width 10 to 15 cm lasts about 22 seconds so that the scanning of the whole body from the heart to the toes takes about 1.5 minutes.

According to the current state of the art, due to the relatively long duration of such scanning by individual sections, the gradual distribution of the contrast agent cannot be exactly monitored. This results in the sections being scanned in different phases of the contrast agent distribution, the images also reflect the contrast agent that is present in the veins. Superimposition of the venous system upon the arterial system makes an angiographic image unusable.

SUMMARY OF THE INVENTION

An object of the present invention is to provide a method for angiographic imaging with MRI technology wherein the above problems are avoided.

The above object is achieved in accordance with the invention by a method for angiographic MRI scanning of a body lying on a table wherein a body layer is excited within a certain section by RF pulse while simultaneously applying a slice-selection gradient in the longitudinal direction of the body so that, at the beginning of the excitation, the section is located on the edge of the homogeneous zone of the magnetic field of the MRI apparatus and its width in the slice-selection-direction is smaller than the maximum possible field-of-view. The section is scanned by the application of a phase-coding gradient in the slice-selection direction as well as a frequency-coding gradient oriented perpendicular to the direction of the phase-coding gradient and in the table plane. The body is uniformly and continuously moved by uniformly and continuously moving the table so that the section to be scanned uniformly moves through the homogeneity range of the magnetic field. The gradient fields are simultaneously, uniformly, and continuously repositioned in response to the motion of the table so that the section to be scanned does not move in relation to the table, and thus to the body, until the section reaches the other end of the homogeneity range of the magnetic field and is completely scanned.

According to the present invention, these steps are repeated so that the homogeneity range of the magnetic field moves in relation to the body until a desired body zone is fully scanned.

In a preferred embodiment of the invention, after the scanning is completed, individual body zones are compiled into a complete image.

According to the invention, after the excitation of the relevant section, the scanning can be performed in various projection directions.

In particular, the projection directions can be scanned frontally and/or 45° coronal-sagittally and/or −45° coronal-sagittally.

The above object also is achieved in accordance with the present invention in a magnetic resonance imaging apparatus operable according to the above-described method.

The above object also is achieved in accordance with the principles of the present invention in a software product, loadable into the control computer of a magnetic resonance apparatus, for operating the magnetic resonance apparatus in the manner described above.

DESCRIPTION OF THE DRAWINGS

FIG. 3 shows the arrangement of gradient fields in a perspective views for angiographic scanning by sections according to the current state of the art.

DESCRIPTION OF THE PREFERRED EMBODIMENTS

Figure 1:
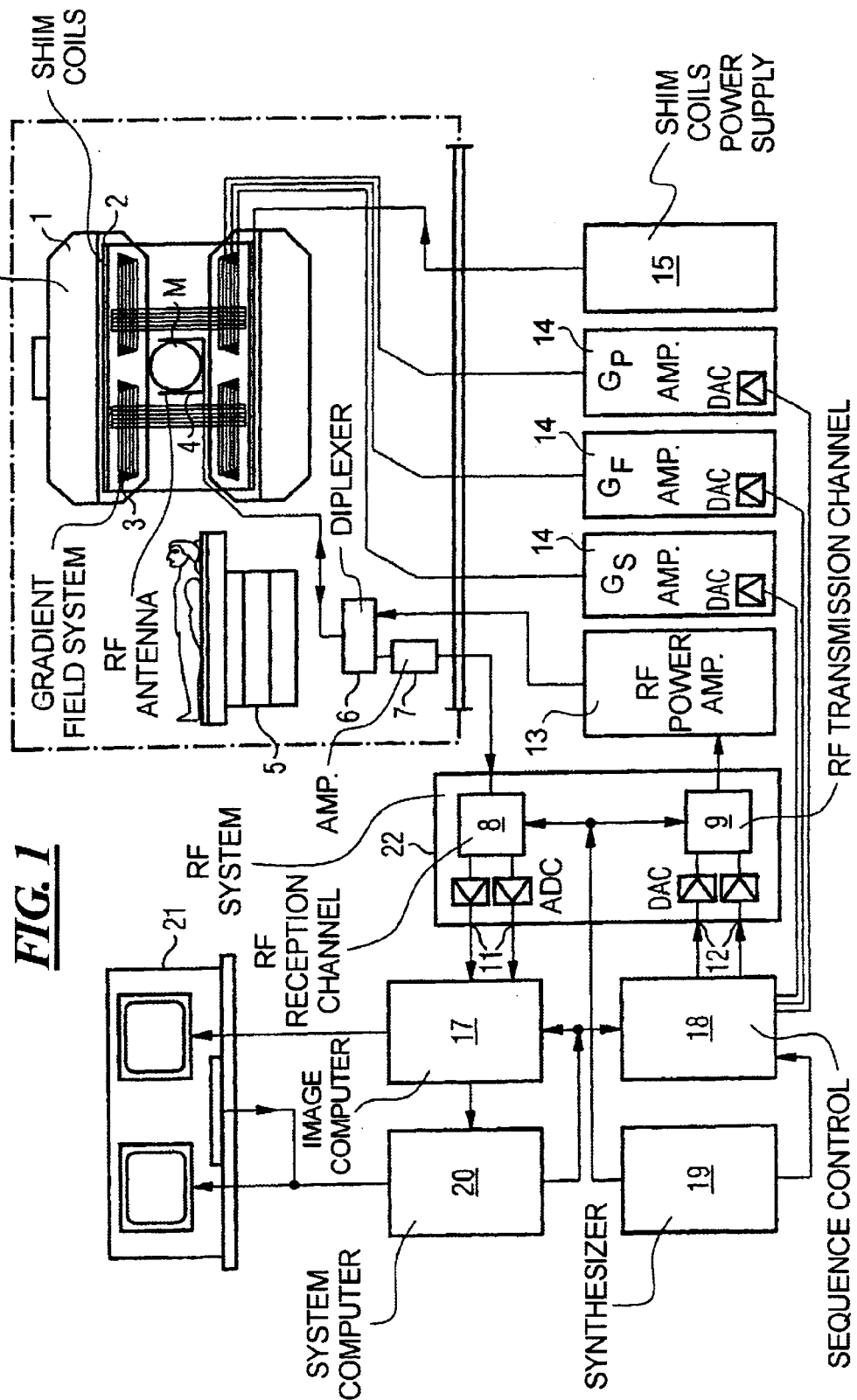
FIG. 1 schematically illustrates a magnetic resonance imaging apparatus operable in accordance with the invention.

FIG. 1 is a schematic illustration of a magnetic resonance imaging apparatus operable with an improved projection angiography acquisition technique according to the present invention. The arrangement of the components of the magnetic resonance imaging apparatus is the same as that of a conventional magnetic resonance imaging apparatus, but it is operable in a non-conventional manner, as described below. A basic field magnet 1 generates a strong, time invariant, basic magnetic field that polarizes, i.e., aligns the nuclear spins in the zone of the object, such as a part of the human body, to be scanned. The high degree of homogeneity of the magnetic field required for magnetic resonance imaging is defined within a sphere-like volume M, into which the relevant region of the patient's body must be brought. In order to meet the homogeneity requirements, and especially to eliminate any time invariant influences, the shim plates (made of a ferromagnetic material) are placed in suitable position. Time-variable influences are eliminated by shim coils 2 that are driven by a shim power supply 15.

A cylindrical gradient coil system 3 that consists of three windings, is integrated in the basic field magnet 1. Each winding is driven by an amplifier 14 to generate a linear gradient field in a defined direction of the Cartesian coordinate system. The first winding of the gradient field system 3 generates a slice-selection gradient $G_L$, the second sub-winding generates a frequency-coding gradient $G_F$, and the third winding generates a phase-coding gradient $G_P$. According to the present invention, in coronary projection, the frequency-coding gradient $G_F$ is oriented left-to-right in relation to the patient, while the two other gradients—the slice-selection gradient $G_L$ and the phase-coding gradient $G_P$—are applied along the longitudinal axis of the body. The reason for this non-conventional arrangement of the gradients according to the invention will be explained in more detail below.

Furthermore, each amplifier 14 includes a digital-to-analog converter that is operated by a sequence control 18 to generate gradient pulses at the right time.

The gradient field system 3 also physically supports a radio-frequency antenna 4 that converts the radio-frequency pulses generated by a radio frequency power amplifier 13 into a pulsating electromagnetic field in order to excite the nuclei and to align the nuclear spins of the object or part of the object to be scanned. The radio-frequency antenna 4 also converts the pulsating electromagnetic field emanating from the nuclear spins (i.e., usually nuclear spin echo signals caused by a pulse sequence consisting of one or more radio-frequency pulses and one or more gradient pulses) into a voltage that is fed through an amplifier 7 into a radio-frequency reception channel 8 of a radio-frequency system 22. The radio-frequency system 22 also includes a transmission channel 9, which generates the radio-frequency pulses that excite the nuclear magnetic resonance signals. In response to a pulse sequence defined by the system computer 20, the relevant radio-frequency pulses are represented in the sequence control 18 digitally, as a sequence of complex numbers. This sequence of numbers is then fed—as real and imaginary parts—through inputs 22 into a digital-to-analog converter in the radio-frequency system 22 and from this converter, into the transmission channel 9. In the transmission channel 9, the pulse sequences are modulated onto a radio-frequency carrier signal, having a base frequency matching the resonant frequency of the nuclear spins in the scanned section.

The switch between transmission and reception occurs by means of a transmit/receive diplexer switch 6. The radio-frequency antenna 4 radiates radio-frequency pulses into the scanned section to excite nuclear spins and then receives the resulting echo signal. The magnetic resonance signals thus obtained are phase-sensitively demodulated in the reception channel 8 of the radio-frequency system 22, and are converted by respective analog-to-digital converters into real and imaginary parts of the measurement signal. Using the magnetic resonance data obtained in this way, a computer 17 reconstructs an image. The system computer 20 controls the obtained magnetic resonance data, image data, and the control programs. Using parameters pre-defined by the control programs, the sequence control 18 controls the generation of the desired pulse sequences and the corresponding scanning of k-space. The sequence control 18 is especially important for controlling the proper switching of the gradients in time, the transmission of radio-frequency signals with the defined phase and amplitude, and the reception of the magnetic resonance signals. The time base for the radio-frequency system 22 and the sequence control 18 is provided by a synthesizer 19. The configuration of the MRI apparatus, the selection of proper control programs to generate a magnetic resonance image, and the display of the produced magnetic resonance image are performed via a terminal (console) 21, which includes a keyboard and one or more monitors.

On the monitor of the terminal 21, the user can retrieve various pop-up folders, through which the user can configure the MRI apparatus as needed. These folders are generated by the system computer 20. They display an input window, via which the user can enter parameters and thus change the settings of the MRI devices. These folders are divided into groups by topic. So, for example, there is a folder for CONTRAST, which allows the user to, among other things, set the flip angle. A ROUTINE folder allows the user to enter the echo time, repetition time, and the number of layers. The RESOLUTION folder is designed to configure the k-matrix. The SEQUENCE file allows the user to select the desired type of sequence (gradient echo sequence, steady-state magnetic echo sequence, true-fisp, EPI, FLASH, etc.).

Especially in the case of angiographic image acquisition, it is important to scan the relevant sections of the body in the correct relation to the point in time when the contrast agent was injected, i.e., in relation to the distribution of the contrast agent in time and space.

Figure 6:
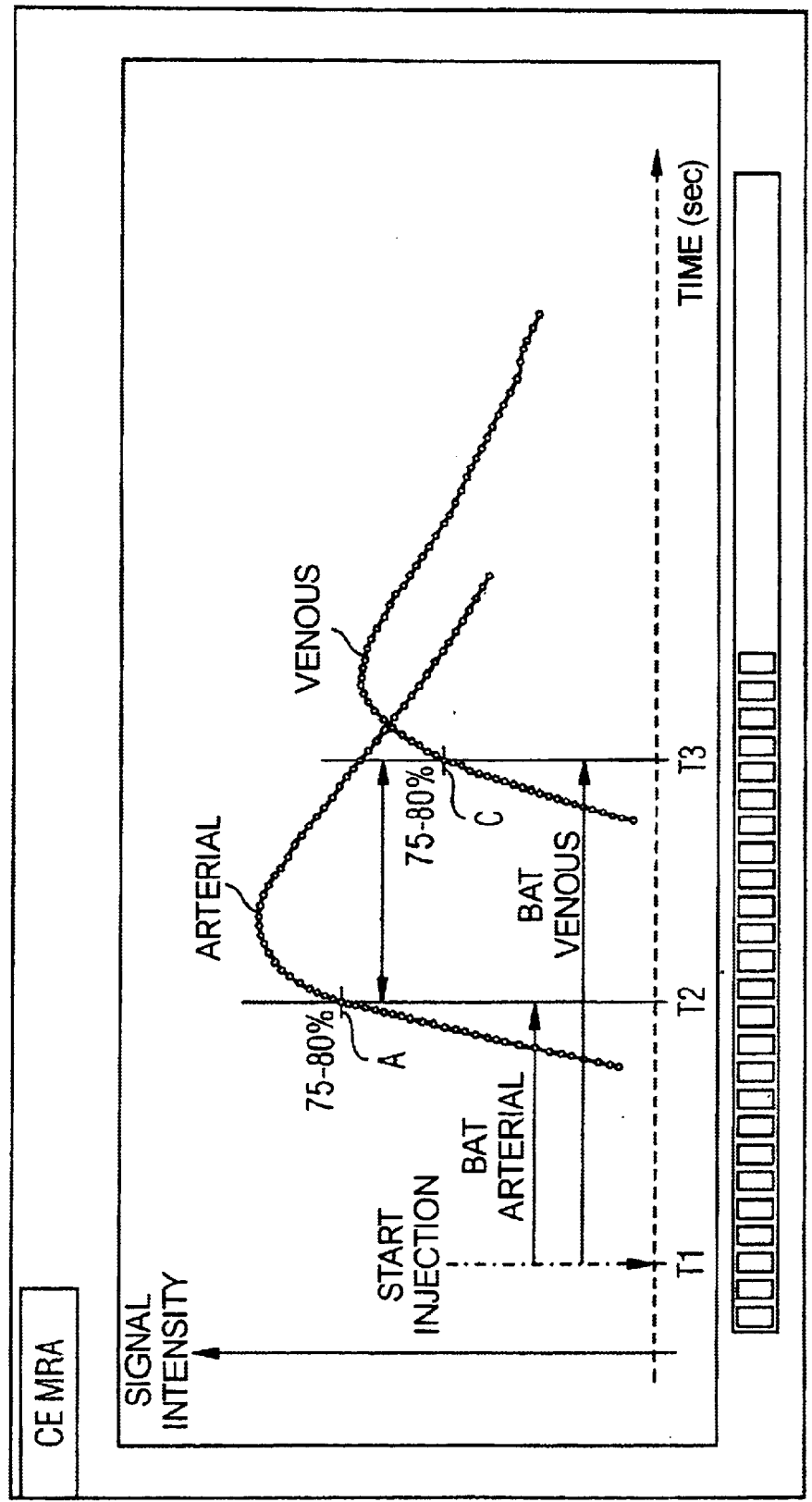
FIG. 6 shows the distribution behavior of the contrast agent in the arterial and venous systems and how it appears over time.

FIG. 6 shows the gradual distribution of the contrast agent in time through the arterial and venous systems within a defined and excited section of the patient's body. After the point in time t1 of contrast agent injection, the signal intensity in the arterial system increases abruptly. The period that lasts until a significant contrast agent enrichment (75–80% of the maximum level) is reached in the arterial vessel system (t1 to t2) is usually called bolus arrival time (BAT). After another interval (t2 to t3), the contrast-agent-enriched blood arrives through capillaries into the venous vessel system, which then also provides a significant signal from the point in time t3 onward.

The influence that the contrast-agent-enriched venous blood can have on the CE MRI scanning has already been discussed. If the actual contrast scanning of selected excited section coincides in time with a significant enrichment of the venous blood, the images of the arterial and the venous systems superimpose on each other and the image that is obtained is of no use.

According to the present invention, the CE MRI scanning is performed in such a manner that the venous contrast agent enrichment in the particular selected section does not provide any significant echo signal. This is the case when the scanning of the excited section is performed within the time interval between the arterial BAT (t2) and the venous BAT (t3) (See FIG. 6).

According to the invention, such an acquisition procedure is implemented so that the conventional magnetic resonance imaging technique is combined with a continuously moving table.

Figure 2:
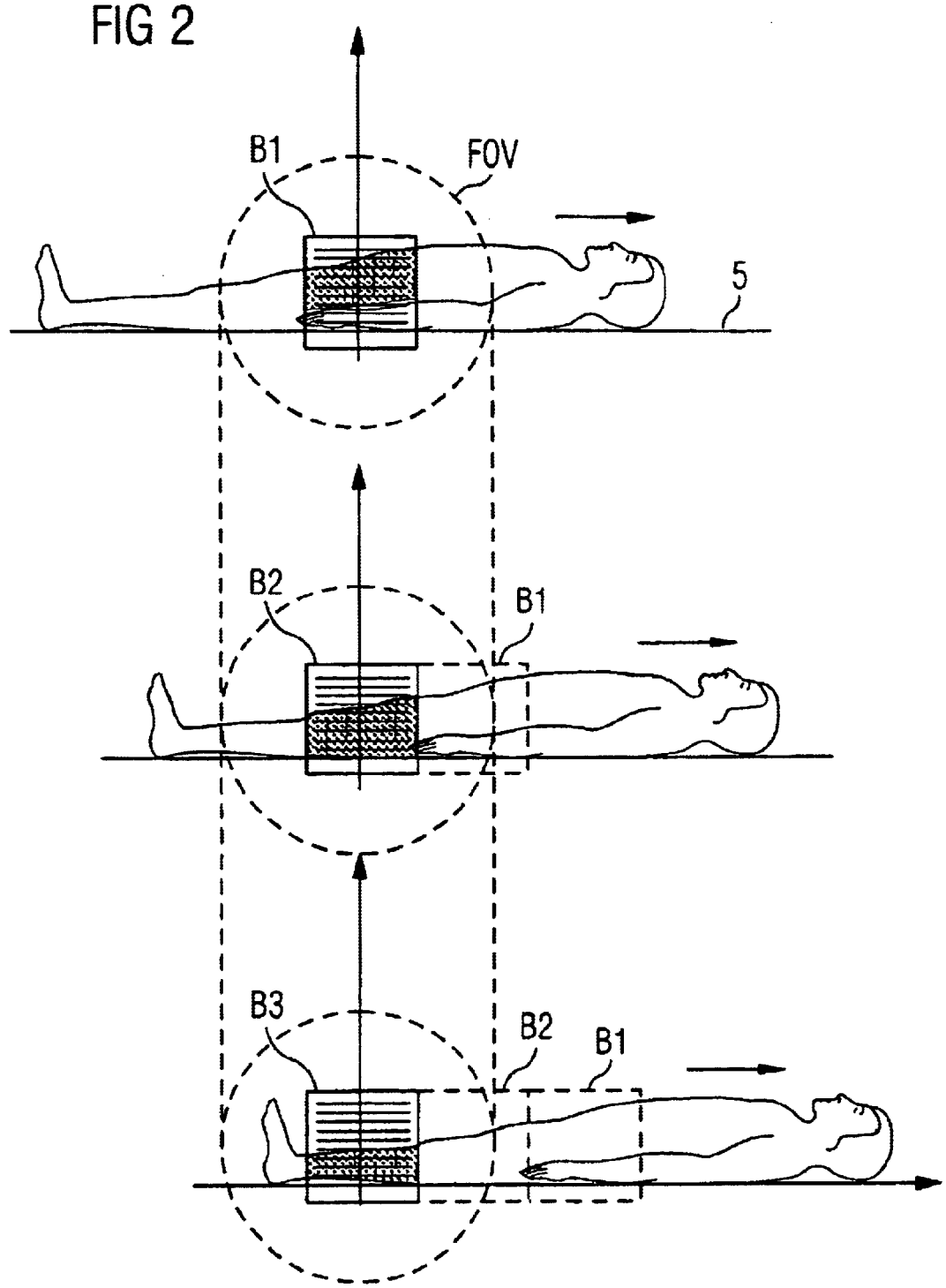
FIG. 2 illustrates 3D angiographic scanning according to the current state of the art.

As previously mentioned, conventional magnetic resonance imaging consists of injecting the patient with a contrast agent, moving the patient step by step, and then scanning and measuring the presence of the contrast in blood section by section. (Before injecting the patient with the contrast agent, so-called native measurements of the zones of interest usually are performed without any contrast agent, which are subsequently compared with the images involving the contrast agent. This procedure allows non-relevant tissue to be eliminated by subtraction). FIG. 2 shows this procedure schematically in a side view of the patient. FIG. 2 shows a patient who is to be examined lying on a table 5, which is moved in three steps relative to the circular range of the homogeneous magnetic field that is indicated with a dashed line. After the patient has been injected with the contrast agent, first a block B1 is excited with an appropriately switched gradient within the field of view; this block containing (in this example) the abdominal part of the body. While the block B1 is being scanned, the table remains at rest. Then, after the scanning has been completed, the table is moved by the width of one block so that the next, immediately adjacent block B2 in the field of view can be excited and scanned. This block includes the upper half of the lower limbs. After this second scanning session, the table is moved again, and block B3, which contains the calves, is scanned.

FIG. 3 shows the result of this conventional magnetic resonance imaging in perspective views. In the conventional procedure, the scanning of one block occurs so that a block of a defined thickness is excited by a slice-selection gradient in, for example, the y-direction. In order to obtain a three-dimensional array of data within this block, the entire block thickness is subdivided—in, for example, the y-direction— into many thin partitions by means of another phase encoding in the y-direction. In this manner, a stack of raw data sets (k-space matrices) is obtained for each block, from which the system computer then reconstructs magnetic resonance images using special image processing procedures. The reason for a left-right phase encoding has to do with reducing the time required for scanning. The phase encoding in the plane vertical to the body plane, which selects the particular layer in the 3D stack, is especially time-consuming and, as a matter of fact, is the most important factor in determining the entire time spent on the MRI of a given block. Currently, the scanning of one block requires about 22 seconds, which is why the scanning process lags behind the progress of the contrast agent in the blood circulation system, and thus why veins become visible in the resulting images.

Figure 4:
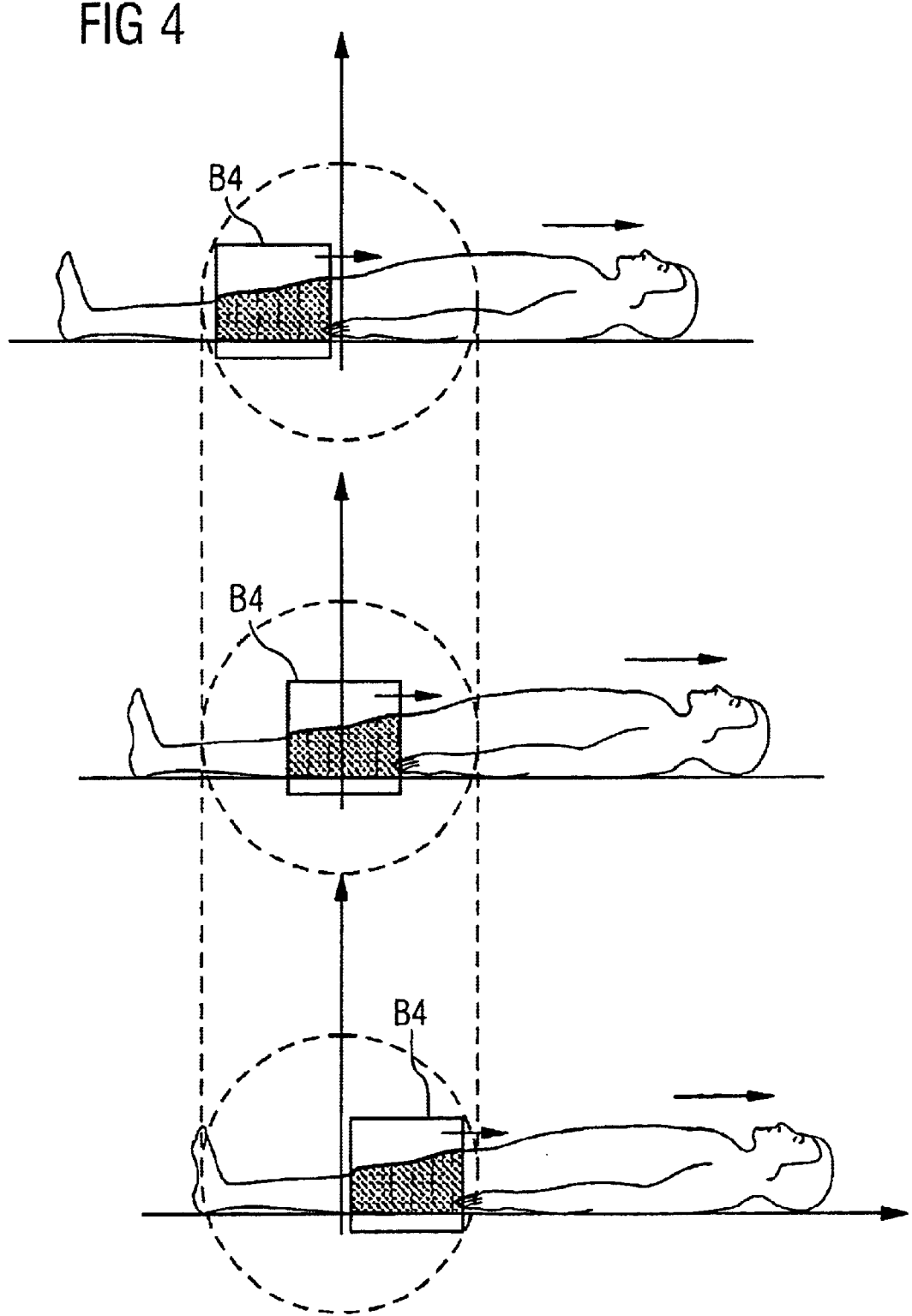
FIG. 4 illustrates angiography scanning according to the present invention.

The present invention is based on a recognition that this problem can be overcome by combining the procedure of the conventional magnetic resonance imaging with a continuously moving table. As shown in FIG. 4, a slice-selection gradient adjacent to the direction of the body length excites a layer B4 that is about 15 cm wide and is visible in the field of view. This layer represents a block, which, in this case, contains the upper part of the patient's thighs. According to the inventive procedure, for scanning the projection of this block B4 after its excitement, the body length direction is used as the phase encoding direction. In the coronary projection direction, the frequency encoding direction is selected from left-to-right transverse to the longitudinal axis of the body and vertically to the perpendicular plane of the lying patient. Since, according to the invention, the slice-selection direction and the phase encoding direction are identical, and thus the field of view to be scanned is known and defined in the phase-coding direction, fold-over image artifacts are advantageously avoided in the phase-coding direction, which substantially reduces the time required for scanning.

Figure 5:
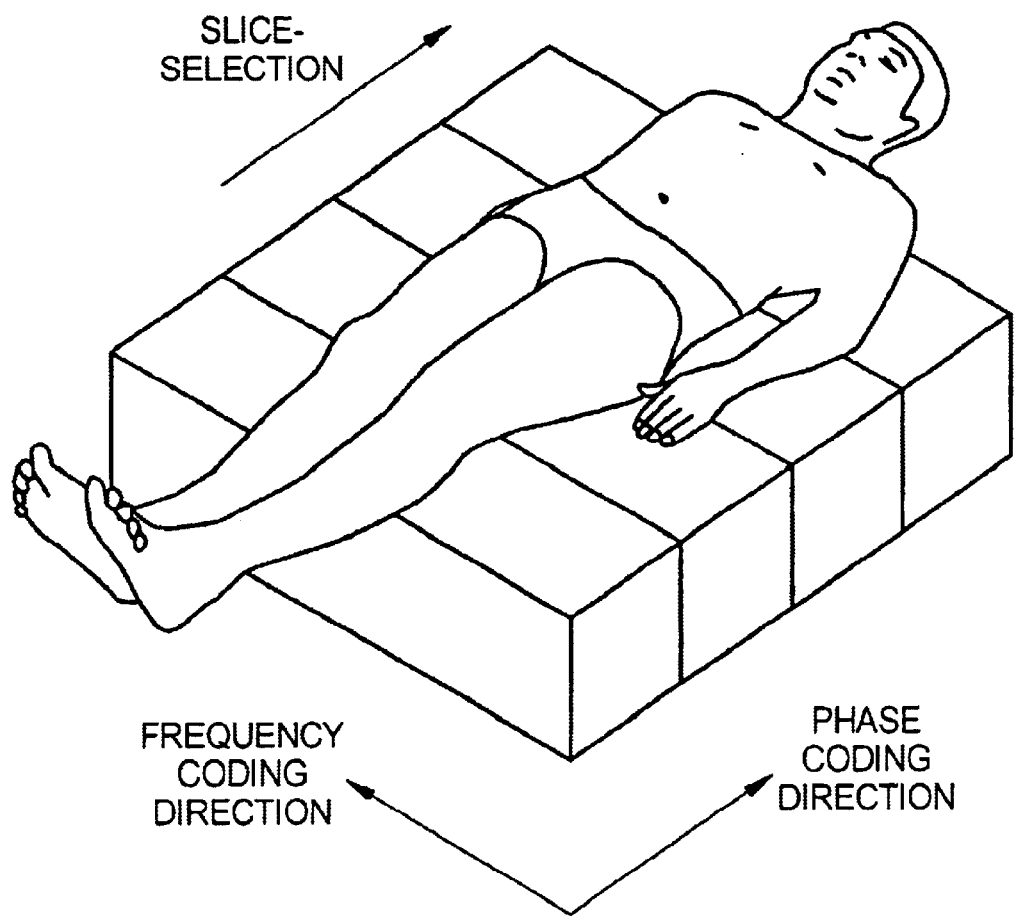
FIG. 5 shows the arrangement of the gradient fields in a perspective view in angiographic scanning of a coronary projection by sections according to the present invention.

Subsequent to the excitation of the block B4, the excited block B4 is quickly (typically about 2.5 seconds per block, per projection) subjected to spatial high-resolution scanning by the sequence control 18 in the projection direction vertical to the body plane. During the scanning of the block, the table 5 is uniformly and continuously moving (about 6 cm/s). In order to prevent any impairment of the image, according to the invention, all three gradient fields (slice-selection, phase-selection, and frequency-coding gradients) are continuously adjusted so that the block being scanned does not move in relation to the body. This effect can be achieved either by suitably offsetting the gradient currents, or by influencing the relevant gradient field with an additional magnetic field generated, for example, by additional coils. In order to guarantee the correct shifting (adjusting) of the gradient fields, the thickness of the block in the z-direction should be smaller than half of the maximum possible field of view (see FIG. 4). In such a manner, projection images of the arterial vessel system are obtained in blocks vertically to the body plane. FIG. 5 shows, in perspective, a representation of the gradient orientation as well as the blocks obtained (in the case of coronary projection direction) according to the procedure of the invention.

An exemplary calculation is provided below to illustrate the procedure according to the invention.

The following calculation relates to a scanner of the type "Magnetom Sonata," which is manufactured by Siemens. This scanner operates with a spherical homogeneity range of the magnetic field with a diameter of 400 mm. It uses a 3D gradient echo sequence of the type "FLASH".

The dimensions of an excitation block in front view are selected to be 350 mm×150 mm. The k-matrix has 1024× 439 pixels in the horizontal plane with a maximum in-plane resolution of 0.342 mm×0.342 mm.

From a pre-defined repetition time of TR=5.0 ms there follows a scanning session duration per block $T_{Block}$ of $T_{Block}$=5.0 ms*439=2.465 s      (per projection)

The maximum imaging length of Δz=140 cm (as defined by the design of the MRI apparatus Magnetom Sonata) allows us to perform 10 scanning sessions (10 blocks, each 15 cm wide) with continuous table motion. From this there follows the duration of the entire scanning process $T_{Total}$=10*2.465 s≈25 s.

The continuous speed of the table motion depends, on both the width of the block (here: 15 cm) and the (in-plane) resolution (here: 100%):

v=15.0 cm/2.465 s=6.09 cm/s

With, for example, 3 projections per block (frontal, +45°, −45°), the speed of the table motion is reduced by the factor 3 accordingly:

v=15.0 cm/3*2.465 s=2.03 cm/s

The following summarizes some of the basic features of the present invention with their advantages:

The uniform continuous table motion allows the arterial contrast agent bolus (contrast agent distribution) to be monitored—e.g., from the aortic arch all the way to the tip of the foot—step by step; this procedure achieves a high resolution in space and time, and it also avoids the overlap of the arterial and venous system images.

The combination of the uniformly continuous table motion with an optimal phase-coding technique allows a substantial reduction in the duration of the entire scanning process. This has, for example, the advantage that the quantity of the contrast agent can be significantly reduced. Furthermore, various projection directions can be scanned within a very short time; for example, we can do 3 projection directions (frontal, +45° coronary-sagittal, −45° coronary-sagittal) in about 3 seconds. In addition, the phase-coding technique of the invention prevents any fold-over image artifacts from arising, for example, in the case of obese patients.

The acquisition technique of the invention is compatible with both IPA (Integrated Panoramic Array) and PAT (Parallel Acquisition Technique), but without special array coils. The system computer can simply merge individual projections. Due to the shifting of the relevant acquisition block in a field of view of about 30 cm in the z-direction, dedicated MRI angiography scanners could contain a shorter magnet, which would result in substantial savings.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for angiographic MRI scanning of a body of a patient lying on a table, using a magnetic resonance imaging apparatus having a basic field magnet that generates a basic magnetic field in a homogeneity volume, said method comprising the steps of:

(a) exciting a slice of said body in a block-shaped volume of the body by excitation with an RF pulse and simultaneous application of a slice-selection gradient switched in a longitudinal direction of the body so that, at a beginning of the excitation, the block-shaped volume is disposed at an edge of said homogeneity volume and with a width of the block-shaped volume in said slice selection direction being smaller than a maximum possible field of view of the excitation;

(b) spatially coding said block-shaped volume by applying a phase-coding gradient in said slice selection direction and applying a frequency-coding gradient in a plane that is vertical relative to the direction of the phase-coding gradient;

(c) uniformly and continuously moving said body by uniformly and continuously moving said table, to move the block-shaped volume uniformly through said homogeneity volume; and (d) simultaneously uniformly shifting said phase-coding gradient and said frequency-coding gradient in conformity with moving the table so that said block-shaped volume exhibits no motion relative to said table and no motion relative to said patient, until said block-shaped volume is disposed at an opposite edge of said homogeneity volume.

2. A method as claimed in claim 1 comprising repeating steps (a) through (d) to move said field of view relative to said body until a predetermined section of the body is scanned in a plurality of block-shaped volumes.

3. A method as claimed in claim 2 comprising combining data respectively for said plurality of block-shaped volumes to produce an image of said body section.

4. A method as claimed in claim 1 comprising the step of, after exciting said block-shaped volume, scanning said block-shaped volume from different directions.

5. A method as claimed in claim 4 comprising selecting said different scanning directions from the group consisting of a frontal direction, a +45° coronal-sagittal direction, and a −45° coronal-sagittal direction.

6. A magnetic resonance imaging apparatus for angiographic MRI scanning of a body of a patient, comprising:

a basic field magnet that generates a basic magnetic field in a homogeneity volume;

an RF system and a gradient system operated by a control computer to excite a slice of said body in a block-shaped volume of the body of the patient by excitation with an RF pulse and simultaneous application of a slice-selection gradient switched in a longitudinal direction of the body so that, at a beginning of the excitation, the block-shaped volume is disposed at an edge of said homogeneity volume and with a width of the block-shaped volume in said slice selection direction being smaller than a maximum possible field of view of the excitation, and for spatially coding said block-shaped volume by applying a phase-coding gradient in said slice selection direction and applying a frequency-coding gradient in a plane that is vertical relative to the direction of the phase-coding gradient; and said control computer uniformly and continuously moving said body by uniformly and continuously moving said table, to move the block-shaped volume uniformly through said homogeneity volume, and simultaneously uniformly shifting said phase-coding gradient and said frequency-coding gradient in conformity with moving the table so that said block-shaped volume exhibits no motion relative to said table and no motion relative to said patient, until said block-shaped volume is disposed at an opposite edge of said homogeneity volume.

7. A computer program product for operating a magnetic resonance imaging apparatus for angiographic MRI scanning of a body of a patient lying on a table, using a magnetic resonance imaging apparatus having a basic field magnet that generates a basic magnetic field in a homogeneity volume, an RF system and a gradient system, said computer program product being loadable into a control computer of said magnetic resonance imaging apparatus and programming said control computer to:

excite a slice of said body in a block-shaped volume of the body by excitation with an RF pulse and simultaneous application of a slice-selection gradient switched in a longitudinal direction of the body so that, at a beginning of the excitation, the block-shaped volume is disposed at an edge of said homogeneity volume and with a width of the block-shaped volume in said slice selection direction being smaller than a maximum possible field of view of the excitation, and to spatially code said block-shaped volume by applying a phase-coding gradient in said slice selection direction and applying a frequency-coding gradient in a plane that is vertical relative to the direction of the phase-coding gradient;

uniformly and continuously move said body by uniformly and continuously moving said table, to move the block-shaped volume uniformly through said homogeneity volume; and simultaneously uniformly shift said phase-coding gradient and said frequency-coding gradient in conformity with moving the table so that said block-shaped volume exhibits no motion relative to said table and no motion relative to said patient, until said block-shaped volume is disposed at an opposite edge of said homogeneity volume.

* * * * *